US008288086B2

(12) United States Patent (10) Patent No.: US 8,288,086 B2
Metzner et al. (45) Date of Patent: Oct. 16, 2012

(54) METHOD FOR OPERATING A TISSUE PROCESSOR, AND TISSUE PROCESSOR

(75) Inventors: Holger Metzner, Hassloch (DE); Udo Herrmann, Leimen (DE); Hermann Ulbrich, Bad Schoenborn-Mingolsheim (DE); Eva Goedecke, Plankstadt (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 506 days.

(21) Appl. No.: 12/606,933

(22) Filed: Oct. 27, 2009

(65) Prior Publication Data
US 2010/0112624 A1 May 6, 2010

(30) Foreign Application Priority Data

Oct. 31, 2008 (DE) .................... 10 2008 054 071

(51) Int. Cl.
*C12M 1/36* (2006.01)
*C12M 3/00* (2006.01)
*C12Q 3/00* (2006.01)
*G01N 33/48* (2006.01)

(52) U.S. Cl. ..... 435/3; 435/40.5; 435/40.52; 435/286.1; 435/287.3; 436/43; 436/50; 436/55; 436/63

(58) Field of Classification Search ............. 435/3, 40.5, 435/40.52, 286.1, 287.3; 436/43, 50, 55, 436/63
See application file for complete search history.

(56) References Cited

U.S. PATENT DOCUMENTS

| 3,889,014 A * | 6/1975 | Kinney et al. ............... 427/2.13 |
| 8,039,262 B2 * | 10/2011 | Konrad et al. ................ 436/55 |
| 2010/0112625 A1 * | 5/2010 | Erben et al. .................... 435/29 |

FOREIGN PATENT DOCUMENTS

| DE | 196 81 647 | 12/1998 |
| EP | 1 793 218 | 6/2007 |
| WO | 97/19379 | 5/1997 |
| WO | 2004059288 | 7/2004 |
| WO | 2005031312 | 4/2005 |

* cited by examiner

*Primary Examiner* — Timothy Vanoy
(74) *Attorney, Agent, or Firm* — Schlee IP International, P.C.; Alexander R. Schlee (57) ABSTRACT

A method for operating a tissue processor and a respective tissue processor for performing this method are described for the processing tissue samples. The tissue processor comprises at least one retort for receiving the tissue samples and at least one container for receiving a process medium. The process medium is transferred at least one of from the container into the retort and from the retort into the container. A value is automatically measured in the course of transferring the process medium, the value representing a characteristic property of the process medium. The process medium is identified based on the value.

8 Claims, 5 Drawing Sheets

METHOD FOR OPERATING A TISSUE PROCESSOR, AND TISSUE PROCESSOR

CROSS-REFERENCE TO RELATED APPLICATION

This application claims the priority of the German patent application DE 102008054071.4 having a filing date of Oct. 31, 2008. The entire content of this prior application DE 102008054071.4 is herewith incorporated by reference.

BACKGROUND OF THE INVENTION

The invention relates to a method for operating a tissue processor, and to the tissue processor. The tissue processor comprises at least one retort for receiving the tissue samples, and at least one container for stocking a process medium.

Biological tissue samples, in particular histological tissue samples, are often required in the fields of human and veterinary medicine, in particular as microscopic prepared specimens for the assessment of cells and their environment. For microscopic inspection, thin sections of the tissue sample must be prepared for assessment under the microscope, in incident or transmitted light, by an expert.

The production of thin sections, for example using a microtome, requires that the tissue sample have a certain strength so that thin, transparent sections having a thickness on the order of micrometers can be produced using a knife. For this purpose, the tissue sample must first pass through a treatment process in which it is fixed, dehydrated, cleared, and then infiltrated with a carrier material, preferably melted paraffin. These processes are often performed successively in a single unit called a "tissue processor"; this tissue processor contains for this purpose a closable process chamber called a "retort" that receives the various reagents, in particular process media, for carrying out the process steps at a suitable temperature and pressure.

One important process step in this context is infiltration of the tissue sample with the carrier material in order to stabilize and consolidate it. This infiltration process step is preceded by a clearing step in which alcohol residues still present from a preceding dehydration step are removed. The chemical solution used for this clearing step is xylene or a similar medium. In the subsequent infiltration step, in which the tissue sample is exposed to the carrier material (usually melted paraffin), xylene constituents that still remain are flushed out and taken up by the liquid carrier material, with the result that the carrier material in the retort becomes contaminated. Residual dehydration reagents are likewise removed during the clearing step. Constituents from the tissue sample itself can also contaminate the dehydration reagents, the clearing reagents, or the carrier material. It is therefore necessary to divide the individual process steps into multiple process substeps in which the tissue sample is exposed successively to a reagent of increasing purity.

If the infiltration process is divided into three process steps, for example, the tissue sample is then first treated, in a first process substep, with a first carrier material that can have a relatively high level of contamination (e.g. with xylene). This is followed, in a second process substep, by a second infiltration step using a second carrier material that has a higher degree of purity than the first carrier material. Lastly, the tissue sample is exposed, in a third process substep, to a third carrier material that has the highest degree of purity; the carrier materials can encompass the same or different reagents. In this fashion the tissue sample is completely infiltrated, in a process of substeps with carrier material of increasing purity, with carrier material that has sufficient quality to produce a good thin section in a microtome, and for a microscopic prepared specimen.

The use of multiple liquid process media having different degrees of purity requires that these process media be kept available in containers in a liquid state. If one of the process media is too highly contaminated, this usually affects the aforesaid first process medium, and it must therefore be replaced with a process medium having an improved degree of purity.

It is an object of the invention to describe a method for operating a tissue processor, and a tissue processor, that contribute in simple fashion to reliable operation of the tissue processor and/or to high quality in the completely processed tissue samples.

This object is achieved by a method for operating a tissue processor that is provided for the processing tissue samples and that comprises at least one retort for receiving the tissue samples and at least one container for receiving a process medium, said method comprising: transferring the process medium at least one of from the container into the retort and from the retort into the container; automatically measuring a measured value in the course of transferring the process medium, the measured value representing a characteristic property of the process medium; and identifying the process medium based on the measured value.

The tissue processor for performing the aforementioned method according to the invention comprises at least one retort for receiving the tissue samples; at least one container for receiving a process medium; a transfer mechanism for transferring the process medium at least one of from the container into the retort and from the retort into the container; an automatic measuring device for measuring a measured value in the course of transferring the process medium, the measured value representing a characteristic property of the process medium; and an identifier for identifying the process medium based on the measured value.

According to the invention, during the operation of a tissue processor a process medium is conveyed from a container into a retort, or from the retort into the container. The tissue processor is provided for the processing of tissue samples. The retort is provided for receiving the tissue samples. The container is provided for stocking the process medium. Upon conveyance of the process medium, a measured value that is representative of a characteristic property of the process medium is automatically acquired. Conclusions can therefore be drawn from the acquired measured value as to the characteristic property, and from the characteristic property as to the process medium currently being conveyed. The characteristic property is, for example, a density and/or a degree of purity of the process medium.

This makes it easy to detect whether the correct process medium for the next process step or process substep has been introduced into the retort, especially when multiple process media and/or process media having different degrees of purity are provided in corresponding containers, and thus contributes to reliable operation of the tissue processor. In other words, it is thereby possible to detect whether a container having one of the process media has been connected in error. It is further possible, without exchanging the erroneously connected container, to use the process medium stocked therein automatically for the correct process step or process substep.

Acquisition of the measured value, and detection, associated therewith, of the process medium being conveyed, furthermore makes it possible to detect, after a process step, whether the process medium is subsequently usable for the same process substep, or whether the process medium is so greatly contaminated that it can be used subsequently for a different process substep or must be replaced.

DETAILED DESCRIPTION OF THE INVENTION

The process medium can be, for example, a fixing reagent, a dehydration reagent, an intermedium, a carrier material, or a cleaning reagent, in particular alcohol or xylene. In this context, "different process media" refers to reagents that are inherently chemically identical and have a slightly different degree of purity, or to reagents that are chemically entirely different. At least one sensor, which is preferably provided between the container and the retort in the flow direction, is provided for acquiring the measured value. If the process media differ from one another in such a way that different sensors are required in order to detect their characteristic properties, a sensor module can be provided that comprises the at least one sensor and corresponding further sensors.

During processing of the tissue sample in the retort, the process medium or media is/are regularly conveyed, in particular pumped, from the corresponding containers to the retort and back again. In this context, they are guided past the sensor in such a way that the latter can acquire the measured value and thus enable a determination of the characteristic property. Acquisition of the measured value is preferably carried out both upon pumping of the process medium to the retort, and upon pumping of the process medium back to the corresponding container.

BRIEF DESCRIPTION OF THE DRAWINGS

Exemplifying embodiments of the invention are explained below with reference to the appended drawings, in which.

DETAILED DESCRIPTION OF THE DRAWINGS

Identical parts are labeled identically in the various Figures.

Figure 1:
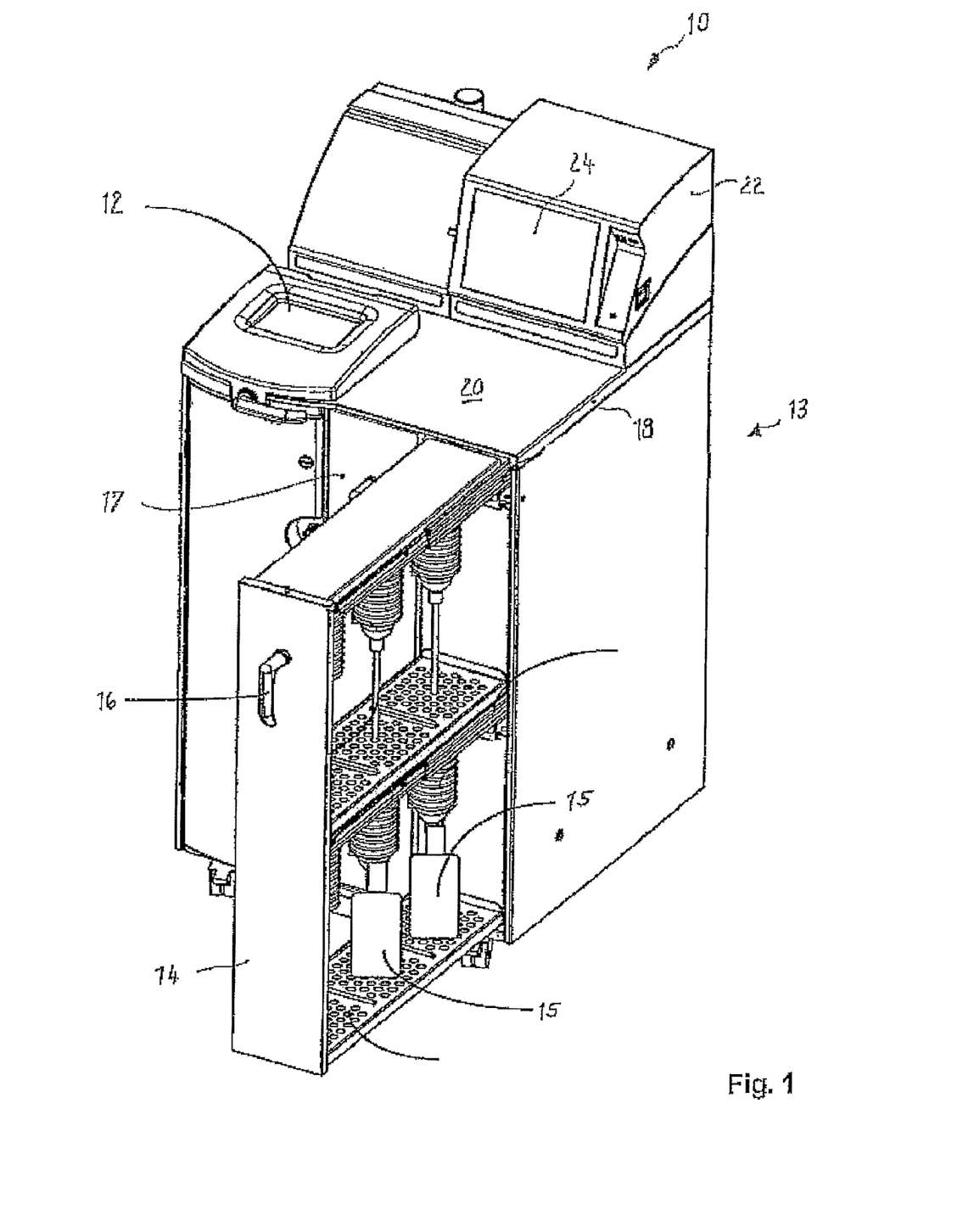
FIG. 1 shows a tissue processor.

FIG. 1 schematically shows a tissue processor 10 with which the method according to the present invention can be carried out. Tissue processor 10 contains a retort 12 for processing tissue samples with different reagents. In said retort 12, the tissue samples pass through multiple process steps. A fixing process, in which formalin is typically used, preferably occurs first. A dehydration process is then accomplished, using alcohol solutions of various degrees of purity. In a subsequent clearing process, alcohol residues are removed from the tissue samples and the tissue samples are prepared for the uptake of carrier material. Xylene or a similar medium is often used in this clearing process. Paraffin or wax of various compositions is preferably suitable as a carrier material. Individual or multiple process steps can be subdivided into process substeps in which the tissue samples are exposed to the aforesaid reagents having different degrees of purity, for example, within one of the process steps, to one of the reagents having an increasing degree of purity.

Once these process steps have been executed, a process of cleaning the retort 12 is carried out using the aforesaid, or further, reagents, for example by performing the aforesaid process steps in reverse order without tissue samples in retort 12.

Tissue processor 10 comprises a cabinet 13 having drawers. One drawer 14 serves for the reception of containers 15 having the reagents (only two of many being shown) that are necessary so that the fixing process, the dehydration process, and/or the clearing process can be carried out. Drawer 14 has a handle 16 for actuation. A further drawer 17 (only partially shown) contains components for the infiltration process described below.

A work area 20 is provided on a desktop 18. Also arranged on desktop 18 is a control device 22 having a screen 24. Control device 22 controls the treatment processes for the tissue samples with the assistance of a computer.

Figure 2:
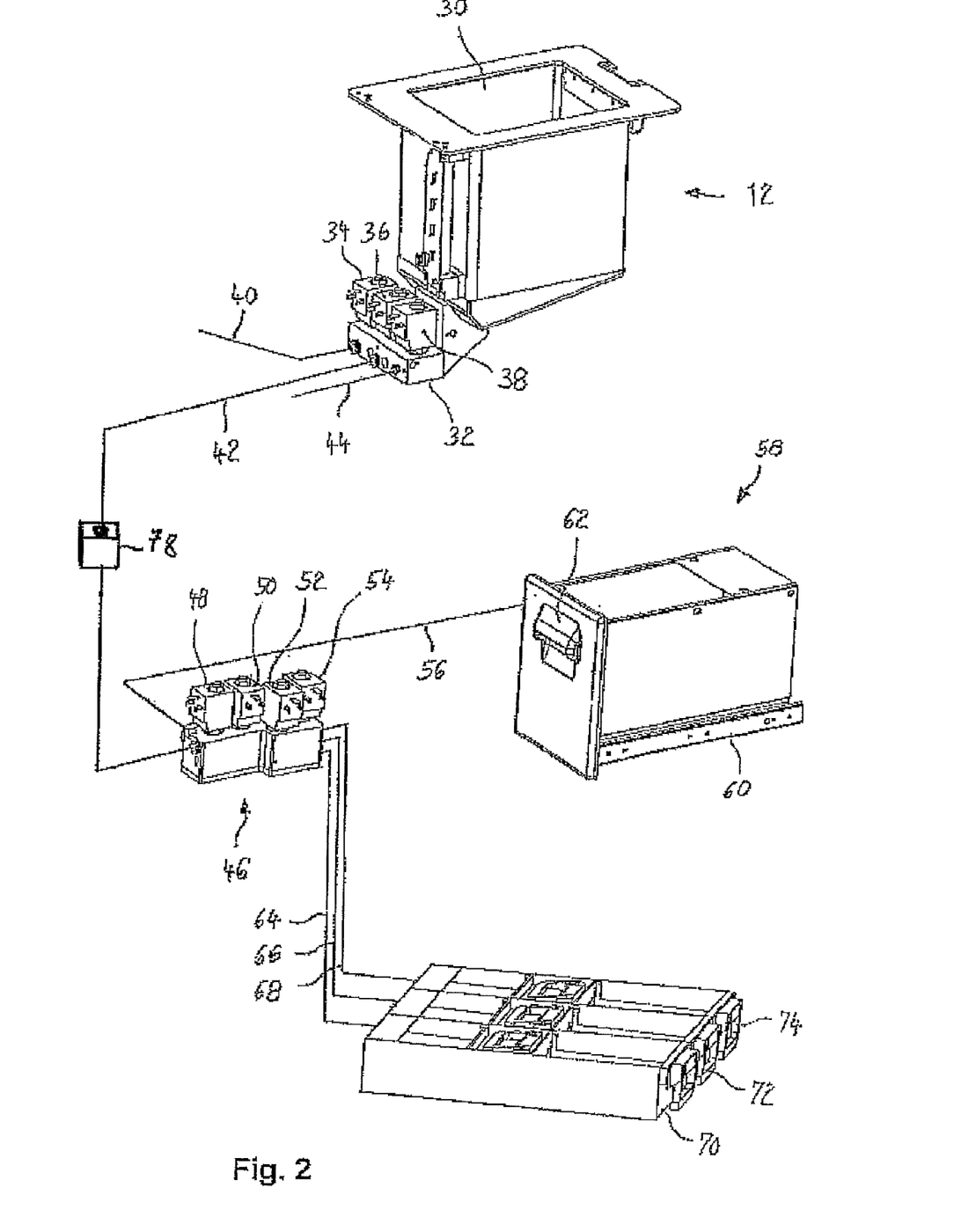
FIG. 2 shows various components of a tissue processor relevant to the infiltration of tissue samples with paraffin.

FIG. 2 shows important components for carrying out the method for infiltrating tissue samples with carrier material, in particular paraffin or wax.

Retort 12 is embodied as a sealable chamber having an opening 30 that can be closed off. Inside retort 12, the various reagents, in particular the paraffin that is important for the infiltration process, can be acted upon by pressure, vacuum, and temperature. The interior of retort 12 is connected via a valve arrangement 32 to lines 40, 42, 44 via electrically controllable valves 34, 36, 38 respectively.

Line 42 is connected via valve 36 to the contents of retort 12. Under the control of valve 36, liquid paraffin is delivered in and back out through line 42. A further line 44 serves for connection to further containers 15 having the reagents for the fixing process, the dehydration process, and/or the clearing process, as will be described below.

Line 42 is connected to a distributor 46 that distributes liquid paraffin under the control of valves 48, 50, 52, 54. Connected to distributor 46 is line 56, which connects the distributor to a supply station 58 for paraffin. Supply station 58 is embodied as a drawer, and contains extension rails 60 and a handle 62.

Also connected to distributor 46 are three lines 64, 66, 68 that connect it to a first container 70, a second container 72, and a third container 74. These containers 70, 72, 74 contain liquid paraffin with an increasing degree of purity. Containers 70, 72, 74 are also configured as drawers, and can be pulled out of the chamber of tissue processor 12 and then removed.

All the lines 40, 42, 56, 64, 66, 68 are heated, as are distributor 46 and, depending on the reagent used, valve arrangement 32 as well, in order to ensure that the paraffin is always kept in a liquid state, e.g. at 65° C., and does not solidify during operation. The same is also true of retort 12 and its parts, and of supply station 58 and containers 70, 72, 74. The corresponding heating elements have been omitted from the Figure for reasons of clarity.

Supply station 58 has a considerably larger volume than the respective container 70, 72, 74. It also serves to melt paraffin that is present in the solid state as paraffin pellets or flakes. The bulk volume of paraffin pellets or flakes is considerably larger than the liquid volume of the melted paraffin for the same weight. The enlarged volume of supply station 58 thus allows a sufficiently large bulk volume of solid paraffin to be introduced, with no need to add more solid paraffin for a sufficient liquid supply. This facilitates the handling of solid paraffin. In addition, the liquid volume of supply station 58 is also sufficiently large that containers 70, 72, 74 can be provided with uncontaminated paraffin for a relatively long operating time, for example even for automatic operation during the night, when operators do not need to be present.

A sensor 78 is arranged between containers 70, 72, 74, and retort 12, in particular between distributor 46 with its valves 48, 50, 52, 54. Sensor 78 is provided for acquisition of a measured value MESS (FIG. 4) that is representative of a characteristic property CHAR of the paraffin, in particular of a degree of purity of the paraffin, that is currently flowing through line 42. It is thus possible, as the paraffin is being pumped to retort 12 and back to containers 70, 72, 74, to ascertain the different degrees of purity of the paraffin currently being used, before and after treatment of the tissue samples. Sensor 78 is, for example, an optical sensor that senses a turbidity or coloration of the paraffin; the paraffin can be treated with a coloring agent in order to ascertain its degree of purity. Alternatively thereto, using sensor 78 it is possible to ascertain a density or a conductivity of the paraffin, as a function of which the degree of purity can then be ascertained.

Figure 3:
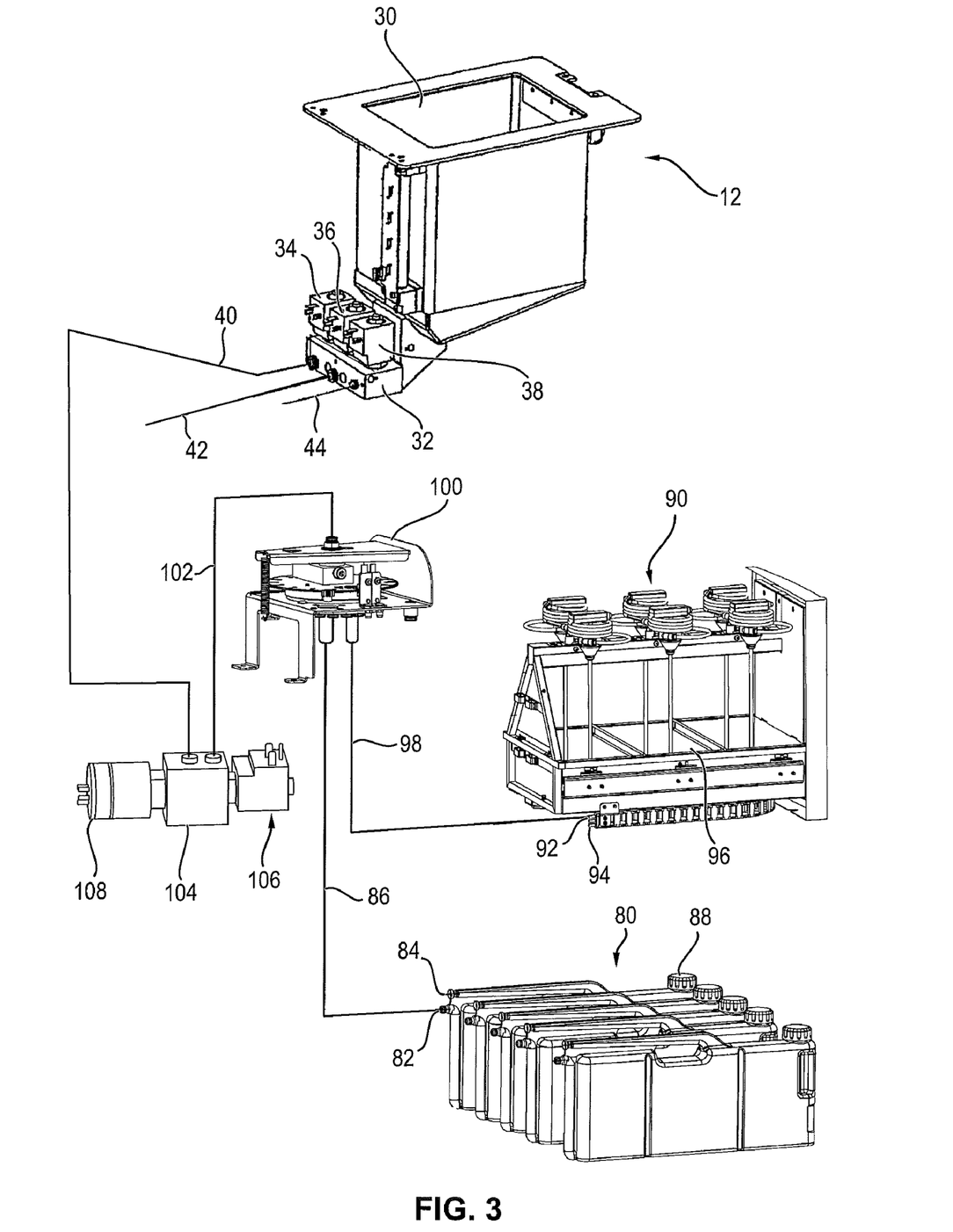
FIG. 3 shows various components of a tissue processor relevant to dehydration, cleaning, or intermediate processing of the tissue samples.

FIG. 3 shows system bottles 80 that each comprise a connector 82 for a line 86 for pumping off a process medium, and a connector 84 for applying pressure to system bottles 80. System bottles 80 furthermore comprise closures 88 through which the process medium can be introduced. System bottles 80 can also be referred to in this context as containers for process media.

What is contained in the different system bottles 80 is, in principle, the chemically identical process medium, the different system bottles 80 each containing the corresponding process medium at different degrees of purity. The process media having different degrees of purity can also be referred to in this connection as different process media.

Further process media having different degrees of purity can be stocked in stations 90 having different baths 96. Stations 90 each comprise a line 92 for transporting the corresponding process medium, and a compressed-air connector 94 for applying pressure to the stations. Connector 92 communicates via a line 98 with a rotary valve 100. Stations 90 can also be referred to in this connection as containers for process media.

Depending on a switch position of rotary valve 100, line 86 or line 98 communicates with line 102 that leads from rotary valve 100 to coupling part 104. A density sensor 106 and a pressure sensor 108 are arranged on coupling part 104. Density sensor 106 and pressure sensor 108 allow the density of the process medium that is currently flowing through coupling part 104 to be sensed. The degree of purity of the process medium can be determined as a function of its density. Density sensor 106 and pressure sensor 108 thus constitute a sensor module for acquiring a measured value that is representative of the degree of purity of the process medium. Density sensor 106 is suitable in particular for ascertaining the degree of purity of alcohol or xylene. It is additionally possible to detect, with the sensor module, whether alcohol, xylene, or paraffin is currently being pumped.

The process media that are stocked in stations 90 or in system bottles 80 encompass, for example, fixing reagents, in particular alkaline fixing reagents, for example formalin; dehydration reagents, in particular alcohols, in particular ethanol; intermedia, for example isopropanol or aromatic compounds, in particular xylene; and/or cleaning reagents, in particular distilled water. In addition, the fixing reagents, dehydration reagents, and/or intermedia can also be used for cleaning and, in this context, can also be referred to as cleaning reagents. One or more other sensors can also be provided alternatively to density sensor 106 or pressure sensor 108. What is important here is that the degree of purity of the respective process medium can be determined with the corresponding sensor. The sensor module preferably comprises exactly as many sensors as there are characteristic properties CHAR ascertainable for all the process media used. Characteristic property CHAR can also, for example, be achieved [sic] by means of a photosensor, a conductivity measurement, and/or by means of a measurement of a pH value of the corresponding process medium.

The tissue samples are then subjected successively to the individual process steps, and thus successively exposed to the different process media. Within the process steps, the tissue samples are exposed successively, within the process substeps, to the process media having different degrees of purity. During treatment with chemically identical process media having a different degree of purity, the tissue samples are exposed to the process media preferably with an increasing degree of purity. In contrast thereto, in order to clean retort 12 the process media can be used in reverse order, in particular with a decreasing degree of purity.

A first program (FIG. 4) is preferably stored on a storage medium of a control apparatus for operating the tissue processor. The program serves, upon pumping of the process medium to retort 12, to automatically determine characteristic property CHAR of the process medium currently being used, and to decide automatically whether the process medium currently being used is suitable for the subsequent process step and/or process substep.

Figure 4:
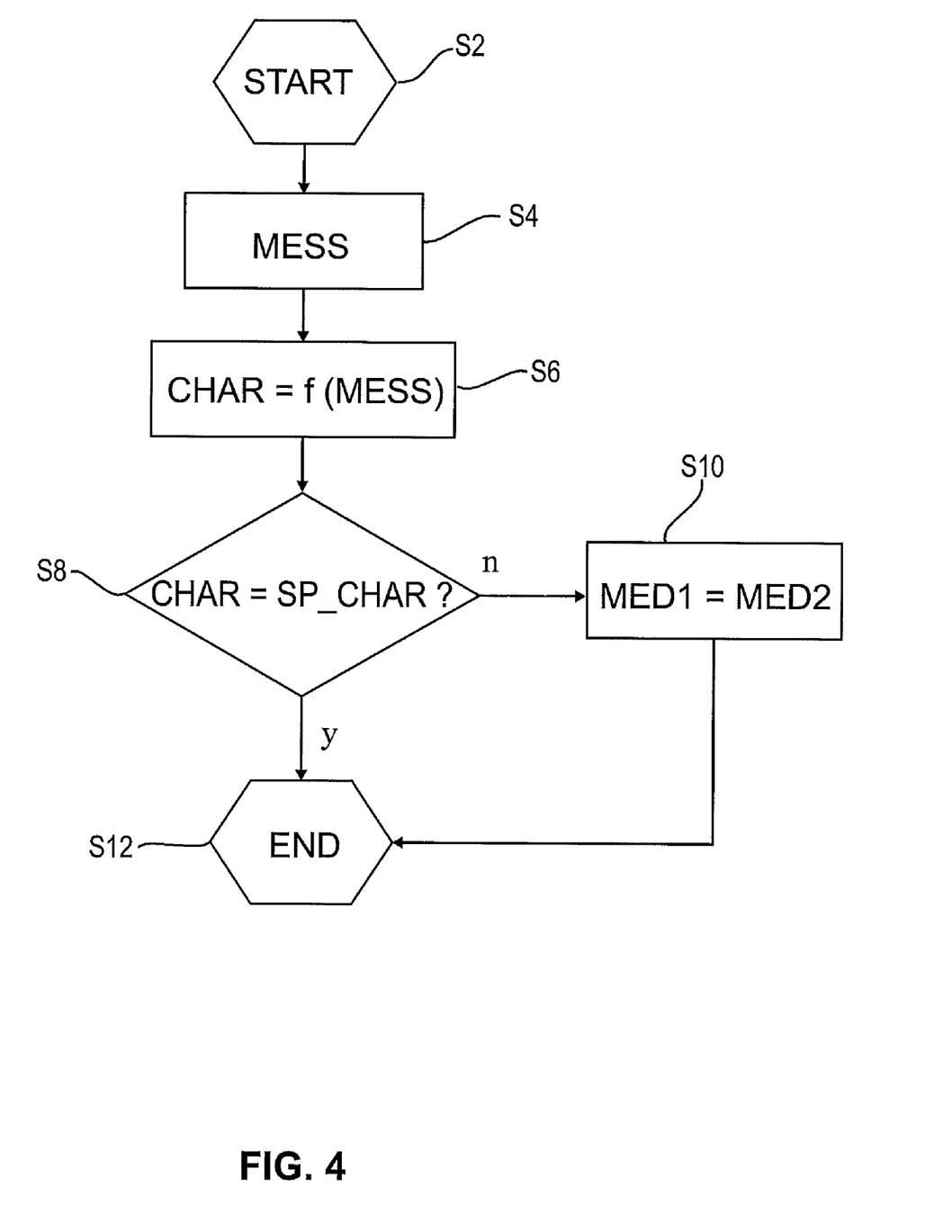
FIG. 4 is a flow chart of a first program for operating the tissue processor.

The first program is preferably started at a step S2 in which, if applicable, variables are initiated, by preference upon pumping of the process medium to retort 12.

In a step S4, a measured value MESS of sensor or sensors 78, 106 is acquired.

In a step S6, characteristic property CHAR is ascertained as a function of measured value MESS. For this purpose, for example, a database can be stored on the storage medium, in which database the various measured values MESS have allocated to them the corresponding characteristic properties CHAR and/or the corresponding process medium.

A step S8 checks whether characteristic property CHAR that has been ascertained corresponds to a predefined target property SP_CHAR. Target property SP_CHAR is predefined, for example, by the subsequent process step or subsequent process substep. In order to carry out the first substep of the dehydration process, for example, a check is made as to whether the process medium pumped to retort 12 is the alcohol having the lowest degree of purity. Alternatively or additionally, in order to carry out the second substep of the clearing process, a check is made as to whether the process medium currently being pumped to retort 12 is xylene of a medium degree of purity. If the condition of step S8 is met, the process medium currently being used then corresponds to the process medium necessary for the subsequent process step or process substep, and processing continues in a step S12. If the condition of step S8 is not met, the process medium currently being used does not correspond to the process medium necessary for the subsequent process step or process substep. The program is then continued in a step S10.

In step S10, pumping of the process medium to retort 12 is interrupted, the process medium is pumped back into the corresponding container, and the process medium is reclassified in accordance with characteristic property CHAR that has been ascertained. The process medium can then subsequently be used automatically for a different process step or process substep with no need to exchange the corresponding container manually, or to manually modify a connector of the corresponding container. In addition, one or more cleaning steps can subsequently be carried out in order to remove, from retort 12 and/or from the lines, the process medium that was erroneously introduced.

The first program can be terminated in a step S12. By preference, however, the first program is executed on a regular basis upon pumping of one of the process media to retort 12.

A second program (FIG. 5) is preferably stored on the storage medium. This program serves, upon pumping of the process medium from retort 12 to the corresponding container, to determine automatically the characteristic property CHAR of the process medium currently being used, and to decide automatically whether the process medium currently being used is still suitable in future for the same process step and/or process substep.

Figure 5:
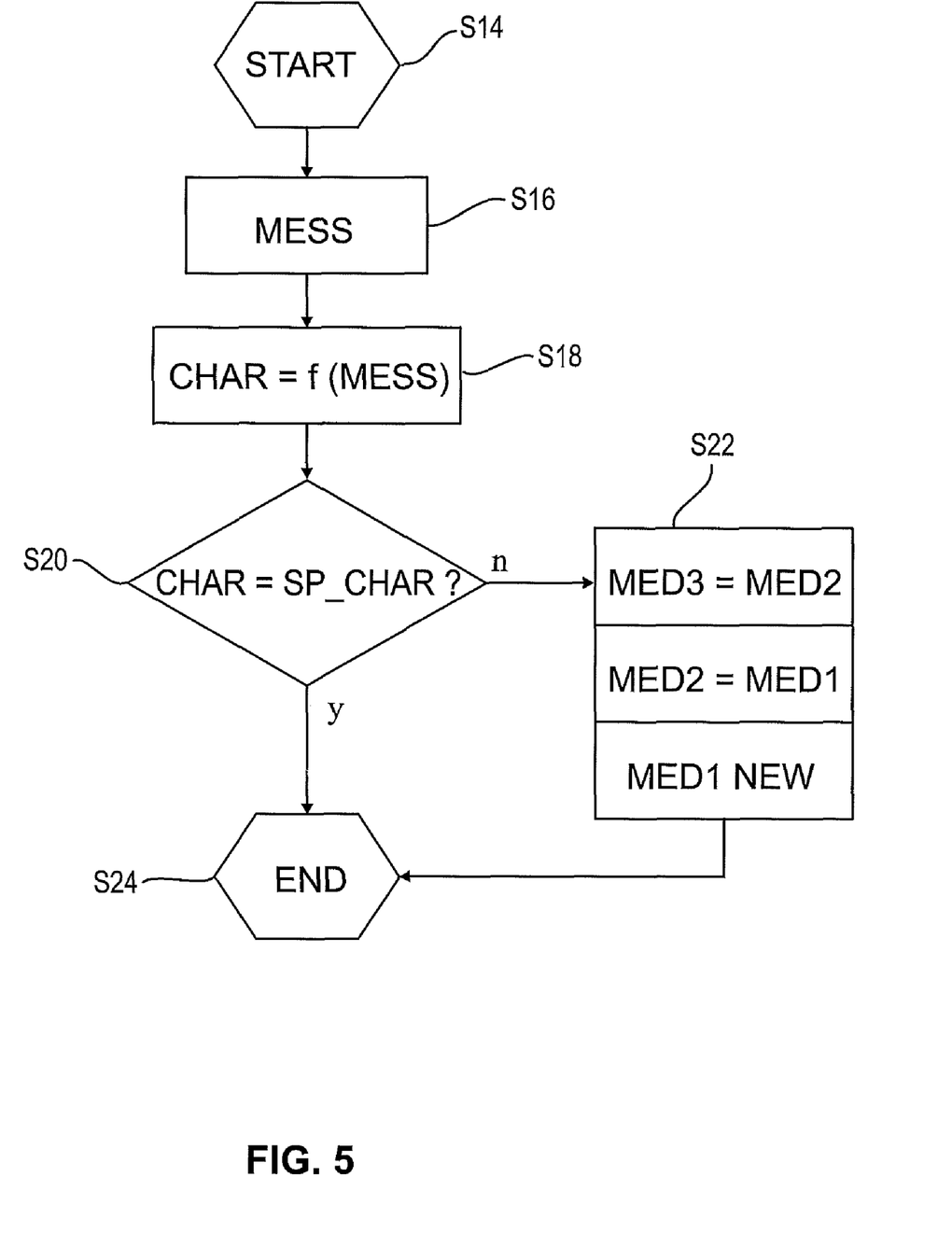
FIG. 5 is a flow chart of a second program for operating the tissue processor.

Steps S14 to S20 of the second program correspond substantially to steps S4 to S8 of the first program, the second program preferably being started in step S14 when the process medium is being pumped from retort 12 to the corresponding container, and a check being made in step S20 as to whether, for example, the process medium currently being used still has the same degree of purity as it did prior to the last process substep that was carried out. If the condition of step S20 is met, the process medium can be used in future for the same process substep, and processing can be continued in a step S24. If the condition of step S20 is not met, the process medium then cannot be used in future for the same process substep, and processing is continued in a step S22.

In step S22, a reordering of the process media occurs, preferably without exchanging the containers or the process media themselves. In particular, a process medium classified as third process medium MED3 is classified as subsequently second process medium MED2, and thus subsequently used no longer for a third of the process substeps but rather for a second of the process substeps. The current second process medium MED2 is classified as subsequently first process medium MED1, and subsequently used for a first of the process substeps. The process medium currently classified as first process medium MED1 is switched out by means of a replenishing instruction NEW and replaced by a new process medium having a highest degree of purity, and subsequently classified as third process medium MED3 and used for the third process substep. The contaminated process media are thus not replaced always by process media having a highest degree of purity, but instead in principle by a process medium having the next-higher degree of purity. In this context, the process media preferably are not moved by pumping, but are merely classified differently.

The second program can be terminated in step S24. The second program is, however, preferably executed again each time the process medium is conveyed from retort 12 back to the corresponding container.

The invention is not limited to the exemplifying embodiments indicated. For example, all the process media can be moved to the retort 12 via only one line, or even more lines can be present for the aforesaid, or further, process media. The number of sensors provided then preferably decreases or increases correspondingly. In addition, the sensors can be arranged very close to the valve, the containers, or retort 12, for example within the same housing. The two programs can moreover be implemented in one program, or subdivided into further subprograms.

LIST OF REFERENCE NUMERALS

10 Tissue processor
12 Retort
13 Cabinet
14 Drawer
15 Reagents
16 Handle
17 Drawer
18 Desktop
20 Work area
22 Control device
24 Screen
30 Opening
32 Valve arrangement
34, 36, 38 Valves
40, 42, 44 Lines
46 Distributor
48, 50, 52, 54 Valves
56 Line
58 Supply station
60 Extension rails
62 Handle
64, 66, 68 Lines
70 First container
72 Second container
74 Third container
78 Sensor
80 System bottles
82, 84 Connectors
86, 98 Lines
88 Closures
90 Stations
92, 94 Connectors
96 Baths
100 Rotary valve
102 Line
104 Coupling part
106 Density sensor
108 Pressure sensor
START Program start
MESS Measured value
CHAR Characteristic property
SP_CHAR Target property
THD Threshold value
MED1 First process medium
MED2 Second process medium
MED3 Third process medium
END Program end
S2 to S12 Method steps

What is claimed is:

1. A method for operating a tissue processor that is provided for the processing tissue samples and that comprises at least one retort for receiving the tissue samples and at least one container for receiving a process medium, said method comprising:
    transferring the process medium at least one of from the container into the retort and from the retort into the container;
    automatically measuring a value in the course of transferring the process medium, the value representing a characteristic property of the process medium; and
    identifying the process medium based on the value.

2. The method according to claim 1, further comprising checking based on the value at least one of a) whether the process medium is present in the container provided for it, and b) whether the container in which the process medium is present is interconnected within the tissue processor as desired.

3. The method according to claim 2, further comprising automatically deciding based on a result of the checking about the processing step for using the process medium for processing the tissue sample.

4. The method according to claim 1, further comprising providing as the characteristic property a degree of purity of the process medium.

5. The method according to claim 4, further comprising storing two or more process mediums in respective two or more containers, each of the processing mediums having a different degree of purity; and automatically deciding based on the determined degrees of purity about the sequence of using the process mediums of different degrees of purity for processing the tissue samples.

6. The method according to claim 1, further comprising providing as the characteristic property a density of the process medium.

7. The method according to claim 1, further comprising providing a process medium that contains at least one of alcohol and xylene.

8. A tissue processor for the processing tissue samples, comprising
- at least one retort for receiving the tissue samples;
- at least one container for receiving a process medium;
- a transfer mechanism for transferring the process medium at least one of from the container into the retort and from the retort into the container;
- an automatic measuring device for measuring a value in the course of transferring the process medium, the value representing a characteristic property of the process medium; and
- an identifier for identifying the process medium based on the value.

* * * * *